(12) United States Patent
Collaueri et al.

(10) Patent No.: US 6,221,393 B1
(45) Date of Patent: Apr. 24, 2001

(54) PHARMACEUTICAL COMPOSITIONS IN THE FORM OF SUSTAINED-RELEASE TABLETS BASED ON HIGH MOLECULAR WEIGHT POLYSACCHARIDE GRANULES

(75) Inventors: Jean-Pierre Collaueri, Bordeux-par-Villevaude; Guillaume Conrath, Chatenay-Malabry, both of (FR); Paul-Joël Derian, Lawrenceville, NJ (US); Gabriel Gousset, Plessis-Robinson; Frédéric Mauger, Changy, both of (FR)

(73) Assignee: Rhodia Chimie, Boulogne Billancourt (FR)

( * ) Notice: Subject to any disclaimer, the term of this patent is extended or adjusted under 35 U.S.C. 154(b) by 0 days.

(21) Appl. No.: 09/425,721

(22) Filed: Oct. 22, 1999

Related U.S. Application Data

(63) Continuation of application No. 08/875,085, filed on Dec. 8, 1997, now abandoned, and a continuation of application No. PCT/FR96/00133, filed on Jan. 26, 1996.

(30) Foreign Application Priority Data

Jan. 27, 1995 (FR) .................................................. 95 00946

(51) Int. Cl.⁷ ............................... A61K 9/22; A61K 9/26
(52) U.S. Cl. .......................... 424/469; 424/465; 424/468; 424/485; 424/488; 514/770; 514/772.3; 514/774; 514/777; 514/781; 514/782; 514/784; 514/951

(58) Field of Search .................................... 424/464, 489, 424/488, 468, 457, 465, 469, 470, 485

(56) References Cited

U.S. PATENT DOCUMENTS

| | | | |
|---|---|---|---|
| 5,077,051 | * 12/1991 | Gallopo et al. | 424/435 |
| 5,662,933 | * 9/1997 | Baichwal et al. | 424/457 |
| 5,902,632 | * 5/1999 | Mehta | 427/214 |

FOREIGN PATENT DOCUMENTS

| | | | |
|---|---|---|---|
| 0 206 368 | 12/1986 | (EP) | C08L/5/00 |
| 0 234 670 | 9/1987 | (EP) | A61K/9/22 |
| 0 360 562 | 3/1990 | (EP) | A61K/9/22 |
| 2 600 267 | 12/1987 | (FR) | B01J/2/16 |
| 87 05212 | 9/1987 | (WO) | A61K/9/22 |
| 93 01803 | 2/1993 | (WO) | A61K/9/16 |
| 94 15643 | 7/1994 | (WO) | A61K/47/36 |

* cited by examiner

Primary Examiner—James M. Spear
(74) Attorney, Agent, or Firm—Jean-Louis Seugnet

(57) ABSTRACT

The present invention relates to a delayed-release pharmaceutical composition which is in the form of tablets prepared by direct tableting and consisting of at least one active principle and a matrix which gives the said composition its delayed-release effect, characterized in that the said matrix consists at least in part of pregranulated polysaccharides of high molecular weight and of synthetic or natural origin.

17 Claims, No Drawings

PHARMACEUTICAL COMPOSITIONS IN THE FORM OF SUSTAINED-RELEASE TABLETS BASED ON HIGH MOLECULAR WEIGHT POLYSACCHARIDE GRANULES

This application is a Continuation application of U.S. application Ser. No. 08/875,085, filed on Dec. 08, 1997 now abandoned, which is an application under 35 U.S.C. Section 371 of International Application Number PCT/FR96/00133, filed Jan. 26, 1996.

The present invention relates to pharmaceutical compositions in the form of sustained-release (also called delayed-release) tablets and to a process for their preparation.

The present invention relates more particularly to compositions of the above type where the tablets are based on polysaccharide granules of high molecular weight, and more particularly on granules of xanthan gum.

The pharmaceutical compositions of the above type contain a pharmacologically active principle and are used when it is desired to administer a medicament to a patient over a prolonged period without requiring the patient to take repeat doses at short intervals.

Direct tableting is a pharmaceutical procedure which is of particular interest since it involves a limited number of operations and constituents and, consequently, requires for its implementation facilities which are less expensive than for a wet-granulation tableting procedure. However, not all pharmaceutical compositions can be obtained by this route.

Natural or synthetic hydrophilic gums, which are polysaccharides of high molecular weight, are known as pharmaceutical excipients, but not all gums can be used in sustained-release compositions in dry tableting procedures. These polysaccharides are of either microbial origin, in which case they are obtained by fermentation of a carbohydrate which can be assimilated by an appropriate microorganism (for example, the xanthan gum obtained from *Xanthomonas campestris*), or natural origin, such as guar gum and carob gum, for example.

Xanthan gums are also excipients which are known for their possible use in the pharmaceutical field, especially for constituting matrices which are intended for the preparation of controlled-release forms. However, hydrophilic gums in general, and xanthan gum in particular, are not used in the pregranulated state.

WO-A 87/05212 teaches the preparation of sustained-release tablets comprising a matrix formed from polysaccharides of natural origin including xanthan gum.

EP-A 234 670 likewise teaches the preparation of sustained-release tablets in which the matrix makes up from 7.5 to 28% by weight of the tablet, the said matrix preferably comprising at least 75% by weight of xanthan gum.

However, the use of non-pregranulated xanthan gum, especially with a high content, i.e. generally a content of approximately 30% by weight relative to the total weight of the tablet, to prepare a tablet by direct tableting, leads to a tablet which has numerous defects, such as splits, heterogeneity, poor mechanical properties, etc.

One aim of the present invention is to prepare a sustained-release tablet based on polysaccharide of high molecular weight, in particular based on xanthan gum, which can be prepared without difficulty by direct tableting and has good properties of release of the active principle and good mechanical properties.

This aim and others are achieved by the present invention, which in fact relates to a pharmaceutical composition in the form of delayed-release tablets which are prepared by direct tableting and consist of at least one active principle and a matrix which gives the said composition its delayed-release effect, characterized in that the said matrix consists at least in part of pregranulated polysaccharides of high molecular weight.

The polysaccharides of high molecular weight which can be used in the context of the present invention include hydrophilic gums, which may be synthetic or natural in origin. High molecular weight polysaccharides of synthetic origin are obtained by fermentation of a carbohydrate in the presence of microorganisms.

By way of natural or modified natural polysaccharides it is recommended to use galactomannans, glucomannans, succinoglycans, scleroglucans, alginates, carragheenans, carob gum, guar gum, cassia gum and tara gum, starch, starch derivatives, pectins, chitosan, and their various possible mixtures. Pregranulated forms of a single polysaccharide or of a polysaccharide mixture can be used. Xanthan gum is the preferred polysaccharide. The term modified polysaccharides according to the invention is intended to mean, more particularly, their chemical derivatives, such as hydroxypropyl derivatives or carboxymethyl derivatives of the gums, for example.

More particularly recommended is the xanthan gum whose preparation is described in numerous publications such as U.S. Pat. No. 3,020,206, U.S. Pat. No. 3,391,060 and U.S. Pat. No. 4,154,654.

It is also recommended according to the invention to use another type of polysaccharide having thickening properties and rheology which are adapted to the same types of application as those of the xanthan gum, these other polysaccharides consisting of succinoglycans whose basic unit contains glucose, galactose and a succinyl radical; they are described in European Patent Application EP-A 351 303 and EP-A 40 445, and in Carbohydrate Research, 73 (1979) pp. 159–168 by Clarence A. Knutson; they can be obtained by microbial fermentation of a medium comprising a carbon source by means of a microorganism belonging to the genus Arthrobacter, such as *Arthrobacter stabiles,* in particular the strain *Arthrobacter stabiles* NRRL-B-1973, to the genus Agrobacterium, such as *Agrobacterium tumefaciens, Agrobacterium radiobacter* or *Agrobacterium rhizogenes,* to the genus Rhizobium, in particular *Rhizobium meliloti* and *Rhizobium trifoli,* to the genus Alcaligenes, such as *Alcaligenes faecalis,* especially the variety myxogenes, or to the genus Pseudomonas, especially the strains Pseudomonas ap. NCIB 11264 and NCIB 11592. Among these succinoglycans, particular mention may be made of the Rheozan® gums described in European Patent Application EP-A 351 303 and obtained by fermentation of a carbon-containing source by means of the strain *Agrobacterium tumefaciens* I-736 deposited in the French National Microorganism Culture Collection (CNCM).

Examples which may be mentioned of commercial polysaccharides which can also be used in the context of the present invention are Wellan®, Chamzan®, Gellan®, Dextran®, Pullulan® and Curdlan®.

The preformed granules entering into the pharmaceutical composition according to the invention are advantageously prepared from a polysaccharide powder, preferably xanthan gum having a particle size distribution which is such that 90% of the particles have a size less than 100 μm, preferably less than 75 μm.

The mean diameter is advantageously between 30 and 60 μm. The term mean diameter is understood to refer to a diameter which is such that 50% by weight of the particles have a diameter which is less than or equal to this diameter.

Numerous processes exist, described in the literature, for preparing polysaccharide granules from polysaccharide powder or from a polysaccharide fermentation solution. Within the context of the present invention it is possible to use any granulation process, such as spray drying, fluidized bed, extrusion, rotating-disc granulation, etc., or any combination of these processes.

Among these known processes mention may be made of U.S. Pat. No. 3,551,133, which describes a process for the preparation of cogranulated forms of xanthan gum and carob gum obtained by spraying an aqueous solution of a powder mixture of the two gums onto inclined-plate or disc granulators.

GB-A 2 086 204 describes a process of the same type.

According to EP-A 206 368, a solution of gums is sprayed onto a fluidized bed of gum.

U.S. Pat. No. 4,557,938 describes the fluidized-bed preparation of granules formed from a mixture of a xanthan gum, guar gum or carob gum with starch.

The preferred granulation process according to the invention is that in which polysaccharide powder, preferably xanthan gum, is sprayed in a fluidized bed with the aid of a stream of gas, water optionally containing a surfactant is sprayed onto the powder, and the granules are obtained by drying. A process of this kind is described in detail in FR-A 2 600 267. According to a preferred variant, all of the excipients of the matrix are cogranulated before being tableted.

In order to prepare the pharmaceutical compositions of the invention, it is recommended to use preformed granules whose mean particle size is between 50 µm and 1000 µm, preferably between 100 and 350 µm, with an apparent density of between 0.3 and 0.8, preferably between 0.35 and 0.7. The polysaccharide may be the sole constituent of the matrix.

However, the matrix may additionally comprise one or more pharmaceutically acceptable excipients, more particularly diluents, cohesion agents, lubricants and colorants, such as, in particular, saccharides such as lactose and sucrose, fatty acids such as stearic acid, for example, polyethylene glycol, dicalcium phosphate, silica, silicoaluminates, cellulose derivatives, gelatin, polyvinylpyrrolidone and the salts of fatty acids, such as magnesium stearate.

The polysaccharide, and more especially xanthan gum, generally forms between 10 and 100% by weight of the matrix, the other excipients preferably being chosen from lactose and dicalcium phosphate. The matrix preferably makes up from 5 to 99.999% by weight of the pharmaceutical composition.

According to a particular embodiment of the invention, the quantity of polysaccharide in the matrix is at least 20% of the total weight of the said matrix.

According to another particular embodiment of the invention, the quantity of polysaccharide in the composition of the matrix is not more than 50% by weight and preferably not more than 40% by weight.

Lactose and/or dicalcium phosphate are the preferred coexcipients. These excipients can be cogranulated, where appropriate, with the polysaccharide or polysaccharides.

In this case the person skilled in the art will have no difficulty in varying the lactose/phosphate ratio in order to obtain the release of the active principle over the desired period of time, being aware that lactose facilitates release, in particular, and that the phosphate tends to have the opposite effect but makes it possible, moreover, to increase the density of the tablets.

According to the invention the proportion of the various ingredients can be varied very widely. Thus it is possible to modulate the release of the active principle very greatly and to pass from quasi-instantaneous release to release over 24 hours or more. Generally, delayed release is desirable in order to reduce the number of daily doses, but it would not be outside the scope of the invention to prepare a quick-release pharmaceutical composition provided that pregranulated polysaccharide were employed in such a composition.

It is also noted that the abovementioned effects of the two preferred coexcipients depend on the quantity of polysaccharide which is present in the matrix. Thus when this quantity is at least 30%, the influence of the lactose and of the dicalcium phosphate is less marked.

For example, when it is desired to obtain a pharmaceutical composition with quick release of an active ingredient, the matrix will more particularly include, in addition to the polysaccharide, a higher proportion of lactose.

On the other hand, if it is desired to obtain a slow-release pharmaceutical composition, i.e. with release over at least 12 hours, the matrix will comprise, in addition to the polysaccharide, a greater proportion of dicalcium phosphate.

The kinetics of release also depend on the nature of the active ingredient and, in particular, on the extent of its solubility in water.

The content of active ingredient in the pharmaceutical compositions of the invention can vary within wide ranges. More particularly it is between 0.001 and 95% by weight of the total composition, the remainder being provided by the matrix. It is preferably between 0.01 and 12% by weight. According to a preferred embodiment, it is advantageously between 0.1 and 10% by weight.

The present invention can be used for the direct tableting of active principles belonging to all classes of medicament which are intended for oral administration. Among the active principles used in compositions according to the present invention, non-limiting mention may be made of nonsteroidal anti-inflammatories and antirheumatics (ketoprofen, ibuprofen, flurbiprofen, indomethacin, phenylbutazone, allopurinol, nabumetone, etc.), opiate or non-opiate analgesics (paracetamol, phenacetin, aspirin, etc.), antitussives (codeine, codethyline, alimemazine, etc.), paychotropic agents (trimipramine, amineptine, chloropromazine and phenothiazine derivatives, diazepam, lorazepam, nitrazepam, meprobamate, zopiclone, and derivatives from the cyclopyrrolone family, etc.), steroids (hydrocortisone, cortisone, progesterone, testosterone, prednisolone, triamcinolone, dexamethasone, betamethasone, paramethasone, fluocinolone, beclomethasone, etc.), barbiturates (barbital, allobarbital, phenobarbital, pentobarbital, amobarbital, etc.), antimicrobial agents (pefloxacin, sparfloxacin, and derivatives from the class of the quinolones, tetracyclines, synergistins, metronidazole, etc.), medicaments intended for the treatment of allergies, antastbmatics, vitamins (vitamin A, vitamin E, D group vitamins, vitamin K), antispasmodics and antisecretory agents (omeprazole), cardiovascular agents and cerebral vasodilators (quinacainol, oxprenolol, propanolol, nicergoline, etc.), cerebroprotective agents, hepatic protective agents, therapeutic agents of the gastrointestinal tract, contraceptives, vaccines, antihypertensives and cardioprotective agents, such as beta blockers and nitro derivatives.

By virtue of the use of polysaccharide in the form of preformed granules, all of the ingredients making up the pharmaceutical composition can be dry-tableted directly, i.e. without using an organic solvent such as ethanol or its mixture with water.

According to the invention, the tableting operation which follows the mixing of the excipients with the active principle is generally carried out under a force which may range from 6 to 10 kN (measured at the tableting roller) and is preferably in the order of 8 to 9 kN. This tableting operation is preferably preceded by prior compression under a force which may range from 0.5 to 2.5 kN.

High tableting rates can be achieved by virtue of the process according to the invention without any detrimental effect, moreover, on the quality of the tablets. In particular it is possible to reach rates greater than 150,000 tablets per hour without causing any splitting.

It is understood that the tablets obtained according to the invention can, if appropriate, be film-coated by conventional methods. The film-coating operation is facilitated by the fact that no splitting occurs during the operation.

The tablets obtained according to the invention have the advantage that the release of the active principle can be modulated, but also have the advantage of good mechanical properties; in particular, the degree of friability is less than 1%.

The fact of starting from a pregranulated polysaccharide, preferably xanthan gum, also has numerous advantages in terms of implementation. Thus it exhibits very good flow properties, which has a favourable effect on the stages of transfer, weighing, mixing and filling of the tableting chambers. Moreover, the perfectly controlled particle size and the absence of fine particles make it possible to restrict the phenomena of separation and the risks linked with fine powders. Moreover, it possesses special tabletability properties, which facilitates the preparation of tablets.

In the text above and below, unless specified otherwise, parts and percentages are by weight.

The invention will be better understood on reading the following working examples which are given by way of illustration and are in no way limiting.

EXAMPLES 1 TO 18

Tablet preparation procedure 700 g of the powder mixture consisting of the active principle (2 g), in this case Aprikalim, and the various constituents of the matrix, namely the pregranulated xanthan gum and, if appropriate, the other excipients, namely dicalcium phosphate and lactose, are mixed beforehand in a mixer of type SONECO®. The powder mixture also contains the lubricant (7 g), namely magnesium stearate, which is thus present in a proportion of 1% by weight in the said powder mixture.

Tableting is carried out under a force of 8.5 kN (measured at the compression roller) using a rotary machine of the MANESTY® type which makes it possible to obtain, from 700 g of powder mixture, 2,000 tablets each of 350 mg, which thus contain 1 mg of Aprikalim. In addition, the powder mixture undergoes precompression under a force of 1.5 kN.

Pregranulated xanthan gum (Rhodigel Easy® marketed by Rhône-Poulenc) is used, where 95% by weight of the granules have a particle size of between 150 and 250 $\mu$m and an apparent density of 0.5 g/cm$^3$, this gum being prepared according to the fluidized-bed technique described, in particular, in French Patent FR-A 2 600 267.

The matrices of Examples 1 to 18 have different excipient contents, which are collated in Table 1 below.

The prepared tablets are measured for the following parameters, the values of which are collated in Table 1 below:

a) Macroscopic appearance of the tablets and evidence of splits:
   −:no splitting,
   +:some splitting,
   ++:significant splitting.

b) The density of the tablets, measured with a helium pycnometer (mean result of measurements carried out on 15 tablets).

c) The wetting angle (in degrees) and the rate of absorption of one drop of 0.1N HCl (representative of a gastric medium), measured with a goniometer and making it possible to evaluate the instantaneous hydration capacity of the tablet.

d) The weight variation coefficient (weight v.c.) of the tablets obtained, measured on 40 tablets.

e) The hardness variation coefficient (hardness v.c.) of the tablets obtained, measured on 15 tablets, and constituting an indicator of splitting in the course of tableting.

f) The kinetics of release of the active principle under "sink" dissolution conditions (volume of the dissolving medium is considered as being infinite) and in a medium having 2 different pH values, namely pH=1.1 for 2 hours followed by pH=6.8 for 8 to 23 hours. The active principle is assayed by HPLC and UV detector. From these assays, the release profile as a function of time is evaluated, as is the duration required for release of 50% by weight of the Aprikalim.

It is clearly evident from Table 1 that the weight variation coefficients are low, which indicates that the tablets obtained on the rotary machine are homogeneous.

It appears, moreover, that when the content of xanthan gum increases this reduces the instantaneous wettability of the tablet and restricts the release of the active principle. The high potentiality of control of the release by xanthan gum is clearly demonstrated by Table 1. Thus, in a time of 30 minutes, release goes from 7.5% to 65% when the content of xanthan gum goes from 100% to 12%. The embodiment of Examples 5 and 6 makes it possible to demonstrate the reproducibility of the dissolution profiles when two batches are produced with the same composition. Generally speaking, a total absence of splitting or a very low tendency to split is observed.

COMPARATIVE EXAMPLE

The procedure of Examples 10 and 17 is repeated precisely except that the xanthan gum granules are replaced by a standard xanthan gum which has not been pregranulated (Rhodigel® marketed by Rhône-Poulenc), having a particle size centred on 100 $\mu$m, containing 40% of fines with a particle size of between 35 and 50 $\mu$m. The powder mixtures exhibit poor tabletability.

Moreover, the tablet production tests were not conclusive, since the tablets obtained did not possess a minimal degree of cohesion and exhibited too great a splitting phenomenon.

TABLE 1

| Ref. Ex. | MATRIX COMPOSITION (Relative proportion of excipients) | | | Wetting angle (in degrees) | WEIGHT v.c. in % | HARDNESS v.c in % | SPLITTING | % by weight of active principle released | | | |
|---|---|---|---|---|---|---|---|---|---|---|---|
| | Xanthan gum | Lactose | Dicalcium Phosphate | | | | | 30 min | 1 h | 3 h | 5 h |
| 1 | 12 | 88 | 0 | 0 | 0.7 | 4 | – | 65 | 78 | 81 | 84 |
| 2 | 12 | 0 | 88 | 0 | 1 | 9 | + | 23 | 35 | 55 | 63 |
| 3 | 12 | 59 | 29 | 0 | 0.6 | 5 | – | 85 | 93 | 96 | 98 |
| 4 | 12 | 29 | 59 | 0 | 0.4 | 8 | – | 51 | 68 | 82 | 85 |
| 5 | 24 | 38 | 38 | 50 | 1.4 | 17 | + | 18 | 25 | 55 | 65 |
| 6 | 24 | 38 | 38 | 54 | 0.9 | 28 | + | 22 | 33 | 57 | 65 |
| 7 | 24 | 25 | 51 | 54 | 0.7 | 40 | + | 17 | 33 | 47 | 52 |
| 8 | 24 | 51 | 25 | 52 | 1.3 | 10 | + | 23 | 34 | 61 | 69 |
| 9 | 36 | 32 | 32 | 54 | 1.1 | 19 | – | 16 | 26 | 46 | 60 |
| 10 | 36 | 64 | 0 | 62 | 1.3 | 15 | + | 19 | 33 | 57 | 65 |
| 11 | 36 | 0 | 64 | 40 | 1.8 | 7 | – | 15 | 24 | 53 | 63 |
| 12 | 36 | 32 | 32 | 44 | 1.4 | 6 | – | 17 | 27 | 50 | 64 |
| 13 | 36 | 32 | 32 | 50 | 1.4 | 3 | – | 16 | 27 | 50 | 65 |
| 14 | 52 | 48 | 0 | 68 | 1.4 | 4 | – | 14 | 22 | 38 | 51 |
| 15 | 52 | 0 | 48 | 42 | 1.7 | 5 | – | 16 | 25 | 42 | 54 |
| 16 | 68 | 0 | 32 | 70 | 1.4 | 3 | – | 12 | 26 | 41 | 51 |
| 17 | 68 | 32 | 0 | 76 | 1.5 | 5 | – | 13 | 21 | 37 | 48 |
| 18 | 100 | 0 | 0 | 80 | 0.8 | 5 | – | 7.5 | 17 | 25 | 30 |

What is claimed is:

1. A delayed-release pharmaceutical composition which is in the form of tablets prepared by direct tableting and comprising one or more active principles and a matrix which gives said composition its delayed-release effect, wherein said matrix comprises a pregranulated polysaccharide, said polysaccharide being a xanthan gum of high molecular weight having a particle size between 50 and 1000 μm, and an apparent density between 0.3 and 0.8.

2. A pharmaceutical composition according to claim 1, wherein the particle size is between 100 and 350 μm and the apparent density is between 0.35 and 0.7.

3. A pharmaceutical composition according to claim 1, wherein the matrix further comprises one or more pharmaceutically acceptable excipients selected from the group consisting of diluents, cohesion agents, lubricants and colorants.

4. A pharmaceutical composition according to claim 1, wherein the matrix further comprises one or more pharmaceutically acceptable excipients selected from the group consisting of saccharide, stearic acid, polyethylene glycol, dicalcium phosphate, silica, silicoaluminate, a cellulose derivative, gelatin, polyvinylpyrrolidone and a salt of a fatty acid.

5. A pharmaceutical composition according to claim 4, wherein the salt of a fatty acid is magnesium stearate.

6. A pharmaceutical composition according to claim 1, wherein the pregranulated xanthan gum is prepared by the fluidized-bed technique.

7. A pharmaceutical composition according to claim 4, wherein the additional excipient is lactose or dicalcium phosphate.

8. A pharmaceutical composition according to claim 6, wherein the xanthan gum forms between 10 and 100% by weight of the matrix.

9. A pharmaceutical composition according to claim 1, wherein the matrix makes up from 5 to 99.999% by weight of the pharmaceutical composition.

10. A pharmaceutical composition according to claim 3, wherein the polysaccharide is cogranulated with the other excipient of the matrix.

11. A process for the preparation of a delayed-release pharmaceutical composition which is in the form of tablets consisting of one or more active principle and a matrix which gives said composition its delayed-release effect, wherein the said process comprises the step of carrying out a direct tableting of a composition comprising one or more active principles and a matrix comprising a pregranulated polysaccharide, said polysaccharide being a xanthan gum of high molecular weight having a particle size between 50 and 1000 μm, and an apparent density between 0.3 and 0.8.

12. A process according to claim 11, wherein the pregranulated polysaccharide is prepared from a xanthan gum powder having a mean particle size of between 30 and 60 μm.

13. A process according to claim 12, wherein the quantity of polysaccharide in the matrix is not more than 40% by weight.

14. A pharmaceutical composition according to claim 1, wherein the content of active ingredient is between 0.001 and 95% by weight of the total composition, the remainder being provided by the matrix.

15. A pharmaceutical composition according to claim 14, wherein the content of active ingredient is between 0.01 and 12%.

16. A pharmaceutical composition according to claim 15, wherein the content of active ingredient is between 0.1 and 10%.

17. A pharmaceutical composition according to claim 1, wherein the active principles are nonsteroidal anti-inflammatories, antirheumatics, opiate analgesics, non-opiate analgesics, antitussives, psychotropic agents, steroids, barbiturates, antimicrobial agents, medicaments intended for the treatment of allergies, antiasthmatics, vitamins, antispasmodics and antisecretory agents, cardiovascular agents, cerebral vasodilators, cerebroprotective agents, hepatic protective agents, therapeutic agents of the gastrointestinal tract, contraceptives, vaccines, antihypertensives or cardioprotective agents.

* * * * *